(12) United States Patent
Richard et al.

(10) Patent No.: US 10,322,978 B2
(45) Date of Patent: Jun. 18, 2019

(54) METHOD FOR PRODUCING 1,3-BUTADIENE FROM 1,4-BUTANEDIOL

(71) Applicants: IFP Energies nouvelles, Rueil-Malmaison (FR); Compagnie Generale des Etablissements Michelin, Clermont-Ferrand (FR)

(72) Inventors: Romain Richard, St Quentin Fallavier (FR); Marc Jacquin, Lyons (FR); Margarita Dorato, Clermont-Ferrand (FR); Nuno Pacheco, Clermont-Ferrand (FR); Claire Rannoux, Clermont-Ferrand (FR)

(73) Assignees: IFP Energies nouvelles, Rueil-Malmaison (FR); Compagnie Generale des Etablissements Michelin, Clermont-Ferrand (FR)

( * ) Notice: Subject to any disclaimer, the term of this patent is extended or adjusted under 35 U.S.C. 154(b) by 0 days.

(21) Appl. No.: 15/552,050

(22) PCT Filed: Feb. 17, 2016

(86) PCT No.: PCT/EP2016/053301
§ 371 (c)(1),
(2) Date: Aug. 18, 2017

(87) PCT Pub. No.: WO2016/131846
PCT Pub. Date: Aug. 25, 2016

(65) Prior Publication Data
US 2018/0037519 A1    Feb. 8, 2018

(30) Foreign Application Priority Data
Feb. 18, 2015    (FR) .................................. 15 51353

(51) Int. Cl.
  C07C 67/08    (2006.01)
  C07C 67/54    (2006.01)
  C07C 1/213    (2006.01)

(52) U.S. Cl.
  CPC .............. *C07C 1/213* (2013.01); *C07C 67/08* (2013.01); *Y02P 20/127* (2015.11)

(58) Field of Classification Search
  None
  See application file for complete search history.

(56) References Cited

U.S. PATENT DOCUMENTS 2,345,113 A    3/1944   Guggemos et al.
2,576,268 A *  11/1951  Shugar ................... C08K 5/103
                                                   106/170.33

(Continued)

FOREIGN PATENT DOCUMENTS

WO    WO-2015088178 A1 *  6/2015  ............... C07C 1/24

OTHER PUBLICATIONS

English Translation of WO2015088178 obtained Mar. 15, 2018 from ESPACNET (Year: 2018).*

(Continued)

*Primary Examiner* — Philip Y Louie
(74) *Attorney, Agent, or Firm* — Millen, White, Zelano and Branigan, P.C.

(57) ABSTRACT

A method for producing 1,3-butadiene from a 1,4-butanediol feedstock:
  One step for esterification of 1,4-butanediol,
  One step for pyrolysis of 1,4-butanediol diester, producing butadiene.

14 Claims, 2 Drawing Sheets

(56) References Cited

U.S. PATENT DOCUMENTS

| | | | | |
|---|---|---|---|---|
| 2004/0044170 A1* | 3/2004 | DeBruin | ............ | B01D 19/0042 |
| | | | | 528/272 |
| 2006/0094894 A1* | 5/2006 | Day | ........................ | C07C 67/60 |
| | | | | 560/180 |
| 2009/0137825 A1* | 5/2009 | Bauduin | ............... | C07C 29/149 |
| | | | | 549/263 |
| 2015/0315335 A1* | 11/2015 | Kang | ..................... | C08G 63/16 |
| | | | | 525/448 |

OTHER PUBLICATIONS

Ping He et al., "Acetylation of Alcohols and Phenols Using Continuous-Flow, Tungstosilicic Acid-Supported, Monolith Microreactors With Scale-Up Capability", J. Flow Chem. 2012, 2, 47-51.
International Search Report Corresponding to PCT/EP2016/053301—Date of Completion: Mar. 15, 2016—dated Mar. 23, 2016.

* cited by examiner

METHOD FOR PRODUCING 1,3-BUTADIENE FROM 1,4-BUTANEDIOL

TECHNICAL FIELD OF THE INVENTION

The invention relates to the production of 1,3-butadiene from 1,4-butanediol.

PRIOR ART

Today, 95% of the production of 1,3-butadiene is ensured by the steam-cracking of hydrocarbons and the subsequent extraction of diolefins within a $C_4$ distillation fraction by extractive distillation methods.

The variation in cost of the raw materials leads to operating steam-cracking units with increasingly lighter but less expensive feedstocks, leading to the reduction in the production of the $C_4$ fraction and consequently of 1,3-butadiene. Alternative methods for producing 1,3-butadiene should therefore be found.

One method for producing 1,3-butadiene from 1,4-butanediol, carried out in Germany at the beginning of the 1940s, is described in the BIOS Final Report No. 1060, German Acetylene Chemical Industry. The method uses a dehydration catalyst that produces 1,3-butadiene from a 1,4-butanediol feedstock. However, this method produces a large majority of tetrahydrofuran (THF) and a small minority of 1,3-butadiene. The THF that is produced is recycled to the catalytic unit to produce more 1,3-butadiene. The recycling of the THF to the catalytic unit is such that this method is not very attractive from an economic standpoint.

Another method for producing 1,3-butadiene from 2,3-butanediol, carried out on a pilot scale in 1945 in the USA, is described in the patents FR 859902, U.S. Pat. No. 2,383, 205, U.S. Pat. No. 2,372,221, and in *Industrial & Engineering Chemistry*, 37 (9), 1945, pp. 865 to 908. This method consists of two primary steps:

The esterification of 2,3-butanediol by a carboxylic acid to form the corresponding diester;

The pyrolysis of diester for producing 1,3-butadiene and carboxylic acid, with the latter being recycled in the esterification step.

This method was developed because the direct dehydration of 2,3-butanediol leads to the large-majority formation of methyl ethyl ketone (MEK) and in contrast to THF, MEK cannot be dehydrated into 1,3-butadiene. This method is particularly advantageous because the step for pyrolysis of 2,3-butanediol diester can be carried out with very good yields (typically more than 80 mol %), and the 1,3-butadiene that is obtained is of high purity (typically more than 99% by weight), which is crucial for its use in various applications (fine chemistry, elastomer).

Nevertheless, this method has certain drawbacks. It is possible to cite the fact that the production of butadiene from 2,3-butanediol with 2,3-butanediol diester as an intermediate compound produces MEK in significant quantities. This MEK is produced both in the step for esterification of diol as well as in the step for pyrolysis of diester. In addition to the loss of material yield, the fact that this impurity is produced on a massive scale poses problems in the separation steps (homogenization of the heterogeneous azeotropic distillation columns) and requires the addition of additional distillation columns dedicated to its elimination.

Furthermore, it is possible to cite the fact that the liquid that is obtained in the step for pyrolysis of 2,3-butanediol diester is a complex mixture that it is difficult to separate to obtain:

The carboxylic acid that it is desired to recycle in the esterification step,

The impurities that it is desired to eliminate from the method,

The intermediate pyrolysis compounds and the unconverted 2,3-butanediol diester that it is desired to recycle in the step for pyrolysis.

In the method for producing 1,3-butadiene from 2,3-butanediol carried out in 1945 in the USA, water was added to the pyrolytic liquid, so as to be able to eliminate—by heterogeneous azeotropic distillation—the impurities, the intermediate pyrolysis compounds, and 2,3-butanediol diester of acetic acid. Thus, the acetic acid that was recovered after this distillation was rich in water and was to be dried within another heterogeneous azeotropic distillation so as to be able to be recycled in the esterification step. The operation for recycling carboxylic acid was therefore difficult and represented a significant part of the operating costs and the investment of the method.

This invention makes it possible to eliminate one or more problems of the prior art. Actually, the applicant discovered that the use of a 1,4-butanediol feedstock made possible an overall improvement of the performances both in the area of the various steps of the method (esterifications, pyrolysis, separations) and in the overall area with simplified recycling, improved management of impurities, and smaller losses.

OBJECT AND ADVANTAGE OF THE INVENTION

The invention relates to a method for conversion that is fed with a 1,4-butanediol feedstock, with said method comprising at least:

a) An esterification step that comprises a reaction section that is fed with the 1,4-butanediol feedstock and a flow that comprises for the most part carboxylic acid, also comprising at least one separation section that separates the effluent from the reaction section into at least one 1,4-butanediol diester effluent, a water effluent, and a carboxylic acid effluent, with said reaction section being implemented in the presence of an acid catalyst at a pressure of between 0.01 and 1.0 MPa and at a molar flow rate of diol feeding said section with a catalyst mol number in said section of between 0.05 and 25 $h^{-1}$;

b) A step for pyrolysis comprising a pyrolysis reactor that is fed with at least said 1,4-butanediol diester effluent that is obtained from the esterification step a), carried out at a temperature of between 500 and 650° C. in such a way as to produce a pyrolysis effluent, with said step for pyrolysis also comprising at least one separation section in which said pyrolysis effluent is cooled to a temperature that is less than 100° C. in such a way as to produce at least one liquid pyrolysis effluent and one vapor pyrolysis effluent, with said vapor pyrolysis effluent being compressed and/or cooled in said separation section in such a way as to condense 1,3-butadiene into a 1,3-butadiene effluent.

One advantage of the invention is to improve the selectivity and the conversion, with esterification and pyrolysis steps, by using a 1,4-butanediol feedstock instead of a 2,3-butanediol feedstock. The improvement of the conversion makes it possible to reduce the investments by reducing the size of the equipment for the same quantity of 1,3-butadiene that is produced. The improvement of the selectivity has a direct effect on the profitability of the method by consuming less butanediol feedstock for the same quantity of 1,3-butadiene that is produced. The improvement of the selectivity also has an indirect effect by producing fewer impurities and therefore reducing the costs associated with the elimination of these impurities. Another advantage of the invention is to facilitate the recycling of the carboxylic acid released in the pyrolysis step to the esterification step by producing a pyrolytic liquid whose various components can be separated by simple distillation, thus reducing the operating and investment costs.

Another aspect of the invention is to increase the overall yield of the method by updating the THF produced during the use of a 1,4-butanediol feedstock.

The applicant has discovered that the pyrolysis of 1,4-butanediol diester could be carried out under the same conditions as that of 2,3-butanediol diester with better conversion and better selectivity, while producing not only fewer intermediate pyrolysis compounds but more upgradeable intermediate pyrolysis compounds in the form of 1,3-butadiene after conversion, making it possible to increase the overall yield of the method by stringing together a series of steps, in particular separation steps, simpler in relation to the methods according to the prior art.

DETAILED DESCRIPTION OF THE INVENTION

Feedstock

In accordance with the invention, the method is fed with a 1,4-butanediol feedstock that comprises at least 90% by weight of 1,4-butanediol. Said 1,4-butanediol feedstock can also comprise water, advantageously at most 10% by weight of water. Said 1,4-butanediol feedstock can stem from a method for fermenting sugars or synthesis gas. Said 1,4-butanediol feedstock can stem from a method for synthesis of 1,4-butanediol from acetylene and formaldehyde.

Step a) for Esterification of 1,4-Butanediol

The conversion method according to the invention comprises an esterification step a) that comprises a reaction section fed with the 1,4-butanediol feedstock, a flow that comprises for the most part carboxylic acid, which advantageously comprises the carboxylic acid effluent that is obtained from the separation section of step a), optionally the liquid pyrolysis effluent or the carboxylic acid flow that is obtained from step b), and optionally an addition of carboxylic acid; said reaction section producing the corresponding diester and water, step a) of the method according to the invention also comprising at least one separation section separating the effluent from the reaction section into at least one 1,4-butanediol diester effluent, a water effluent, and a carboxylic acid effluent, with the latter advantageously able to be recycled into the carboxylic acid supply of the reaction section.

Flow comprising for the most part carboxylic acid is defined as this flow that comprises more than 50% by weight of carboxylic acid.

In a particular arrangement of the method according to the invention, said flow that comprises for the most part carboxylic acid consists of said carboxylic acid effluent and said liquid pyrolysis effluent that is obtained from step b).

In a preferred manner, the carboxylic acid that is used is selected from among formic acid, acetic acid, propanoic acid, butanoic acid, or benzoic acid. In a very preferred manner, the carboxylic acid that is used is acetic acid.

Said reaction section can be produced by any method that is well known to one skilled in the art. It is implemented in the presence of an acid catalyst, which can be homogeneous or heterogeneous. The MMH in the reaction section, i.e., the molar flow rate of diol feeding said section with the catalyst mol number in said section, is between 0.05 and 25 $h^{-1}$, preferably between 0.15 and 20 $h^{-1}$. It is carried out at a pressure of between 0.01 and 1.0 MPa, in a preferred manner between 0.05 and 0.2 MPa, and in a very preferred manner between 0.08 and 0.12 MPa.

Said heterogeneous acid catalyst is, in a non-limiting manner, an ion-exchange acid resin (such as Amberlyst, Amberlite, Dowex, and in particular an Amberlyst 35, an Amberlyst 36, or an Amberlyst 70), a mixed oxide ($ZrO_2$, SnO), or an acid zeolite (H-MOR, H-MFI, H-FAU and H-BEA).

In a preferred manner, said heterogeneous acid catalyst is stable at a temperature that is higher than 130° C., in a preferred manner higher than 150° C., and in a very preferred manner higher than 170° C.

The acid catalysts that are used to catalyze the esterification reaction also activate the dehydration reactions, in particular at high temperatures such as those cited above. In the method according to the invention where a 1,4-butanediol feedstock is used, THF is thus produced by dehydration.

In accordance with the invention, said step a) comprises at least one separation section that separates the effluent from said reaction section into at least one 1,4-butanediol diester effluent, a water effluent, and a carboxylic acid effluent.

In a preferred manner, the reaction section of the esterification step is implemented in a reactive distillation column, into which the 1,4-butanediol feedstock is introduced into the upper part of the column, and the carboxylic acid is introduced into the lower part of the column. The ratio of molar flow rates of 1,4-butanediol and carboxylic acid is between 2 and 6, in a preferred manner between 2 and 4, and in a very preferred manner between 2 and 3.5.

Said reactive distillation column produces—at the top—a distillate that consists primarily of water produced by the esterification reaction and carboxylic acid introduced in excess and—at the bottom—a residue that consists primarily of 1,4-butanediol diester and optionally carboxylic acid. This conversion step is such that the conversion of 1,4-butanediol into 1,4-butanediol diester is greater than 95 mol %, preferably greater than 99 mol %.

In the preferred arrangement where the esterification step comprises a reactive distillation column, if the acid catalyst is homogeneous, it is introduced into the upper part of the column with the 1,4-butanediol feedstock; if the catalyst is heterogeneous, it is kept in the reactive distillation column using a device that is well known to one skilled in the art.

The temperature of the distillation column is encompassed between the boiling point of the water that is produced at the top and that of 1,4-butanediol diester that is produced at the bottom. In the case where the carboxylic acid that is used is acetic acid, the temperature between the top and the bottom of the distillation column typically varies between 100 and 230° C.

The impurities obtained from the dehydration of 1,4-butanediol are eliminated at the top of the reactive distillation column, with the water that is produced and the carboxylic acid that is introduced in excess.

In the preferred arrangement where the esterification step comprises a reactive distillation column, the distillate of said reactive distillation column comprises the water that is produced by the esterification reaction, the carboxylic acid introduced in excess, and the by-product obtained from the dehydration of the 1,4-butanediol feedstock (THF). This distillate is separated into a water effluent, free of carboxylic acid, and which is eliminated from the method, and a carboxylic acid effluent, free of water, and which is advantageously recycled to the reaction section. This separation can be carried out by any method that is well known to one skilled in the art. In a preferred manner, in the case where the acetic acid is used to carry out the esterification of 1,4-butanediol, this separation is carried out by heterogeneous azeotropic distillation using a driver. In a non-limiting way, this driver can be isopropyl acetate, diethyl ether, or else ethyl tert-butyl ether.

A THF effluent that comprises the THF that is produced is advantageously separated from the effluent of said reaction section, advantageously from said distillate of said reactive distillation column, by any means known to one skilled in the art, such as distillation, liquid-liquid extraction, adsorption, to prevent its accumulation in said separation section.

The applicant has discovered that the kinetics and the thermodynamics of esterification of 1,4-butanediol were more favorable than that of 2,3-butanediol. The esterification step a) of the 1,4-butanediol feedstock according to the invention therefore makes it possible to reduce the dwell time in said reaction section, advantageously in said reactive distillation column, as well as the quantity of carboxylic acid introduced, in comparison to the esterification step of the prior art using a 2,3-butanediol feedstock. This difference in reactivity between the two butanediols and the nature of the by-products that are generated allows, within the scope of the method according to the invention, more compact equipment and simplified recycling management.

Step b) for Pyrolysis of 1,4-Butanediol Diester

The conversion method according to the invention comprises a step for pyrolysis that comprises a pyrolysis reactor that is fed with at least said 1,4-butanediol diester effluent that is obtained from the esterification step a), carried out at a temperature of between 500 and 650° C. in such a way as to produce a pyrolysis effluent, with said step for pyrolysis also comprising at least one separation section in which said pyrolysis effluent is cooled to a temperature that is lower than 100° C. in such a way as to produce at least one liquid pyrolysis effluent, which is advantageously recycled in the esterification step a) and a vapor pyrolysis effluent.

The pyrolysis reaction can be implemented with or without the presence of a catalyst.

The pyrolysis reaction primarily transforms 1 mol of 1,4-butanediol diester into 1 mol of 1,3-butadiene and thus releases 2 mol of carboxylic acid. Primarily is defined as more than 70 mol % of 1,4-butanediol diester being converted into 1,3-butadiene. Preferably, more than 80 mol % of 1,4-butanediol diester is converted into 1,3-butadiene. Said pyrolysis reactor, also called pyrolysis oven, is operated at a temperature that is advantageously between 400 and 700° C., preferably between 500 and 650° C., preferably between 550 and 600° C., and in a preferred manner between 575 and 585° C. The optimal contact time within the pyrolysis oven is based on the partial pressure of 1,4-butanediol diester injected into the pyrolysis oven. It is typically 1 second for a partial pressure of diol diester of 0.1 MPa, and 7 seconds for a partial pressure of diol diester of 0.04 MPa. The contact time is defined as the ratio of the reaction volume of the reactor to the volumetric flow rate of feedstock, with the volumetric flow rate being calculated under the temperature and pressure conditions of the reaction medium.

In accordance with the invention, the effluent that is obtained from said pyrolysis reactor is cooled quickly to a temperature that is less than 100° C., preferably less than 50° C., in such a way as to limit the formation of degradation products by, for example, Diels-Alder reaction of 1,3-butadiene on itself to form vinylcyclohexene (VCH). The cooling of the effluent generates a liquid phase and a vapor phase that can be easily separated within a gas-liquid separator tank into a liquid pyrolysis effluent and a vapor pyrolysis effluent.

Said vapor pyrolysis effluent comprises more than 90% by weight, preferably more than 95% by weight, of 1,3-butadiene (without considering the optional inert diluent used to lower the partial pressure of 1,4-butanediol diester within the pyrolysis oven). Said vapor pyrolysis effluent can also contain light organic compounds, obtained from the pyrolysis of the carboxylic acid, such as, for example, in the case where the carboxylic acid is acetic acid, methane, carbon monoxide, carbon dioxide, ketene, hydrogen, or else ethane. Said vapor pyrolysis effluent can be compressed and/or cooled in such a way as to condense 1,3-butadiene into a 1,3-butadiene effluent. The non-condensable organic compounds obtained from the pyrolysis of carboxylic acid are thus eliminated at the top of a gas-liquid separator in the form of an effluent composed of light compounds. Said 1,3-butadiene effluent can then undergo one or more final purification steps that are well known to one skilled in the art. It is possible to cite in a non-limiting manner the purification on a sieve or on a clay; a washing with water follows a drying step. This makes it possible to eliminate the last traces of impurities and to obtain a 1,3-butadiene effluent, which comprises more than 99%, in a preferred manner more than 99.5%, of 1,3-butadiene.

Said liquid pyrolysis effluent consists for the most part of carboxylic acid. The most part is defined as at least 50% by weight, and preferably at least 70% by weight. It can also comprise other organic compounds, such as, for example, unconverted butanediol diester, intermediate pyrolysis compounds (i.e., 1,4-butanediol diester molecules that have lost one carboxylic acid fragment of the two that are required for 1,3-butadiene to form), and optional by-products.

In the method according to the prior art where a 2,3-butanediol feedstock and acetic acid are used, numerous intermediate pyrolysis compounds and impurities are produced. In the case where acetic acid is used for carrying out the esterification of 2,3-butanediol, the pyrolytic liquid comprises 2,3-butanediol diacetate (1.5% by weight), intermediate pyrolysis compounds such as methyl vinyl carbinol acetate (MVCA, 0.8% by weight), methyl ethyl ketone enol acetate (MEKEA, 2.4% by weight), and crotyl acetate (CA, 3.3% by weight) and by-products, such as VCH (2.2% by weight), MEK (1.4% by weight), or methyl acetyl acetone (MAA, 0.9% by weight). These intermediate compounds have a boiling point that is close to that of acetic acid and form homogeneous azeotropes (maximum and minimum) with the latter. The purification of acetic acid for the purpose of its recycling in the esterification step therefore cannot be done by simple distillation. It is necessary to carry out a heterogeneous azeotropic distillation by using water as a driver. In addition to the fact that this operation is complex, it produces a water-rich acetic acid flow that cannot be directly sent back to the esterification step. This water-rich acetic acid flow should therefore be sent back to a second heterogeneous azeotropic distillation so as to eliminate the water. Furthermore, this operation produces an oil that contains unconverted 2,3-butanediol diacetate, intermediate pyrolysis compounds, and by-products. The recovery of products that can be upgraded within this oil is problematic in this regard as well because, i.a., unconverted 2,3-butanediol diacetate and MAA are very difficult to separate by simple distillation.

Surprisingly enough, the pyrolysis of 1,4-butanediol diester leads to a much more limited number of intermediate pyrolysis compounds and by-products, taking into account the improvement of the conversion and the noted selectivity. In the preferred case where acetic acid is used for carrying out the esterification of 1,4-butanediol, the pyrolytic liquid comprises—as a single intermediate pyrolysis compound—3-buten-1-ol acetate with less than 4% by weight, and even less than 1% by weight, and—as by-products—traces of VCH and THF.

The liquid pyrolysis effluent obtained by the method according to the invention contains only a single intermediate pyrolysis compound that has a boiling point that is close to that of carboxylic acid and that forms a homogeneous azeotrope with the latter. This azeotrope is rich in 3-buten-1-ol ester.

In an advantageous manner, said liquid pyrolysis effluent is purified in such a way as to produce a carboxylic acid flow that comprises carboxylic acid from which impurities are removed.

In an embodiment of the invention, the purification of the carboxylic acid can be carried out by simple distillation of the liquid pyrolysis effluent, producing a carboxylic acid flow, and a 3-buten-1-ol ester flow (carboxylic acid azeotrope/3-buten-1-ol ester) that can be recycled in the step for pyrolysis with 1,4-butanediol diester or that can undergo a dedicated pyrolytic treatment.

In another embodiment of the invention, the purification of carboxylic acid can be carried out by pressure-change distillation. The increase in pressure makes it possible to make the azeotrope disappear and to increase the boiling point difference between carboxylic acid and 3-buten-1-ol ester. There is thus obtained, on the one hand, a carboxylic acid flow, and, on the other hand, a pure 3-buten-1-ol ester flow that can be recycled in the step for pyrolysis with 1,4-butanediol diester or that can undergo a dedicated pyrolytic treatment.

Advantageously, said flow that comprises for the most part carboxylic acid that feeds the reaction section of said step a) consists of said carboxylic acid effluent that is obtained from the separation section of said step a) and said carboxylic acid flow produced by one or the other of these embodiments (purification of the carboxylic acid carried out by simple distillation or carried out by pressure-change distillation).

The purification of the liquid pyrolysis effluent for the purpose of its recycling to step a) is therefore greatly simplified in the method according to the invention in comparison to the method according to the prior art.

In another embodiment of the invention, the liquid pyrolysis effluent is directly sent back to step a), taking into account its high level of purity of carboxylic acid, without a carboxylic acid purification step.

Optional Step c) for Conversion of THF

In a preferred arrangement, the method according to the invention also comprises a step c) for conversion of THF that is fed with said THF effluent that is advantageously produced in the separation section of step a), and an acid anhydride effluent, carried out in the presence of an acid catalyst, in which THF is converted into 1,4-butanediol diester by acetolysis.

Actually, the THF effluent that is advantageously recovered within said separation section of said step a) can be transformed into 1,4-butanediol diester by making it react with acid anhydride in the presence of an acid catalyst. The acid anhydride used in this step c) for conversion of THF advantageously corresponds to the carboxylic acid that is used in step a) for carrying out the esterification of 1,4-butanediol. For example, in the preferred mode of the invention where acetic acid is used for transforming 1,4-butanediol into 1,4-butanediol diacetate in the conversion step a), acetic anhydride will advantageously be used in step c) for conversion of THF. This reaction for conversion of THF can be carried out with or without solvent. In a preferred mode of the invention, the solvent that is used is the carboxylic acid that is used in the conversion step a), provided that the latter has been dried in advance, because water would react with acid anhydride.

This step c) for conversion of THF can be carried out continuously or, if the quantity of THF that is produced is small, sequentially ("batch" implementation, in English terminology).

This optional step c) of the invention makes it possible, via a low acid anhydride consumption, to not have THF by-product to be eliminated from the method and to increase the overall yield of the method in 1,3-butadiene, in contrast to the method of the prior art that produces MEK in a large quantity, which cannot be upgraded into 1,3-butadiene.

Furthermore, the addition of acid anhydride makes it possible to carry out the addition of carboxylic acid that is necessary for compensating for losses of carboxylic acid in the pyrolysis step b). Actually, from a purely stoichiometric standpoint, 1 mol of THF and 1 mol of acid anhydride provide 1 mol of 1,4-butanediol diester in step c) for conversion of THF. This mol of 1,4-butanediol diester is then sent, directly or indirectly, to a step for pyrolysis, where from a purely stoichiometric standpoint, 1 mol of 1,4-butanediol diester provides 1 mol of 1,3-butadiene and 2 mol of carboxylic acid. In practice, acid anhydride is introduced in excess in relation to THF in such a way as to ensure an almost-total conversion of the latter and to take into account the fact that the THF effluent that is obtained from the separation section of step a) is not completely anhydrous. The traces of water in THF will therefore consume a portion of the acid anhydride introduced in step c), to produce 2 mol of carboxylic acid.

The conversion of THF into 1,4-butanediol diacetate is described in, for example, Tetrahedron Letters, 45(35), pp. 6599-6602 and in Journal of Heterocyclic Chemistry, 37(5), pages 1351-1353. THF is converted into 1,4-butanediol diacetate in acetic acid, in the presence of an acid catalyst and acetic anhydride, with the acid catalyst able to be, for example, sulfamic acid or sulfuric acid, at a temperature of between 20° C. and 80° C., for a period that ranges from 2 hours to 25 hours. Conversion yields of more than 97 mol % are attained.

In one embodiment of the invention, the effluent that is obtained from step c) for conversion of THF into 1,4-butanediol diester is sent directly to step b) for pyrolysis of 1,4-butanediol diester or else undergoes a dedicated step for pyrolysis, for the purpose of producing more butadiene.

In another embodiment of the invention, the effluent that is obtained from step c) for conversion of THF into 1,4-butanediol diester is sent back to step a) for esterification of the 1,4-butanediol feedstock. This effluent is advantageously introduced into the lower part of said reactive distillation column, optionally with carboxylic acid.

The effluent that is obtained from step c) contains 1,4-butanediol diester, acid anhydride that is not consumed, optionally carboxylic acid that is used as solvent or produced by hydrolysis of the acid anhydride, and a small proportion of unconverted THF and is free of the least trace of water. The effluent that is obtained from step c) can therefore be sent back into said reaction section of said step a), advantageously into said reactive distillation column, without degrading the performance thereof and even makes it possible to improve it.

Actually, THF and carboxylic acid are the lightest elements and migrate toward the top of said reactive distillation column, whereas acid anhydride and 1,4-butanediol diester are the heaviest elements and migrate toward the bottom of said reactive distillation column. Thus, the acid anhydride in step c) that is not consumed for conversion of THF reacts with the very small fraction of 1,4-butanediol monoester and the unconverted 1,4-butanediol traces at the bottom of said reactive distillation column making it possible, all other things being equal, to improve the conversion of the 1,4-butanediol feedstock into 1,4-butanediol diester in step a).

Furthermore, depending on the quantity of acetic anhydride that is not consumed in step c) and that is sent back to step a), the adjustments (i.e., reboil rates, reflux rates, ratio of the 1,4-butanediol feedstock flow rates to the acetic acid flow rate, . . . ) of said reactive distillation column can be adapted for the purpose of reducing the energy consumption of step a). Actually, the variation of the energy consumption of step a) is not linear with the conversion of the 1,4-butanediol feedstock, with the latter % of conversion being more difficult to obtain for a balanced reaction. The use of unconverted acid anhydride in step c) for producing the last % of conversion of the 1,4-butanediol feedstock therefore makes it possible to greatly reduce the energy consumption of step a).

Figure 1:
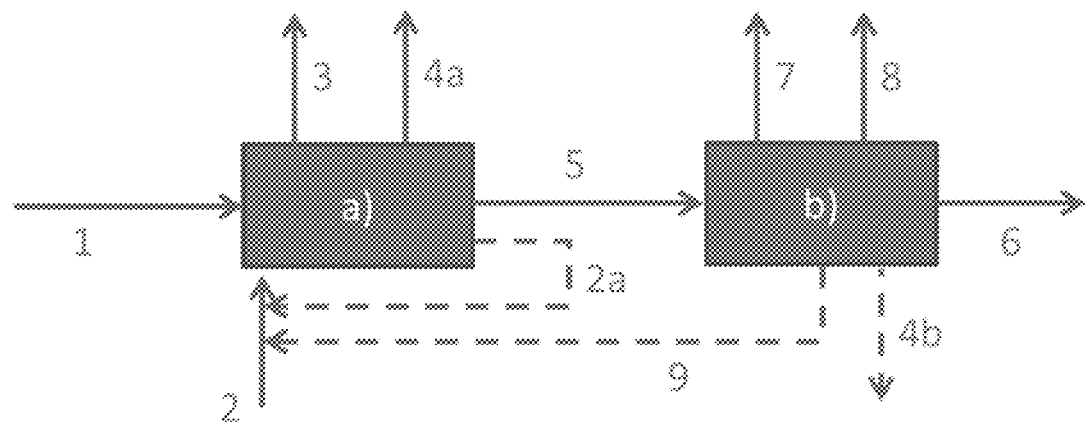
FIG. 1 presents a diagrammatic view of a specific arrangement of the method according to the invention.

The 1,4-butanediol feedstock (1) undergoes a first esterification step a) with a flow of carboxylic acid (9) and a flow that comprises for the most part carboxylic acid (2) to produce a water effluent (3), a 1,4-butanediol diester effluent (5), and a carboxylic acid effluent (2a). During step a), a small fraction of the 1,4-butanediol feedstock is converted into THF, which is eliminated from step a) in the THF effluent 4a). The carboxylic acid effluent (2a) is recycled in a mixture with the flow that comprises for the most part carboxylic acid (2).

The 1,4-butanediol diester effluent (5) feeds a pyrolysis step b) that produces a 1,3-butadiene effluent (7) and a liquid pyrolysis effluent (9) that is recycled to the esterification step a). During the pyrolysis step b), a very small fraction of 1,4-butanediol diester is converted into THF, which can optionally be eliminated from step b) in the 3-buten-1-ol ester effluent 4b) or sent via the flow (9) to step a) ultimately to be eliminated from step a) by the flow 4a).

Furthermore, during the pyrolysis step b), a small fraction of carboxylic acid is cracked. The cracking products are eliminated from step b) in the effluent composed of light compounds (8). The addition of carboxylic acid (2) introduced in step a) compensates for the losses of carboxylic acid in step b). A small proportion of coke is also produced, which is evacuated via the coke effluent (6).

Figure 2:
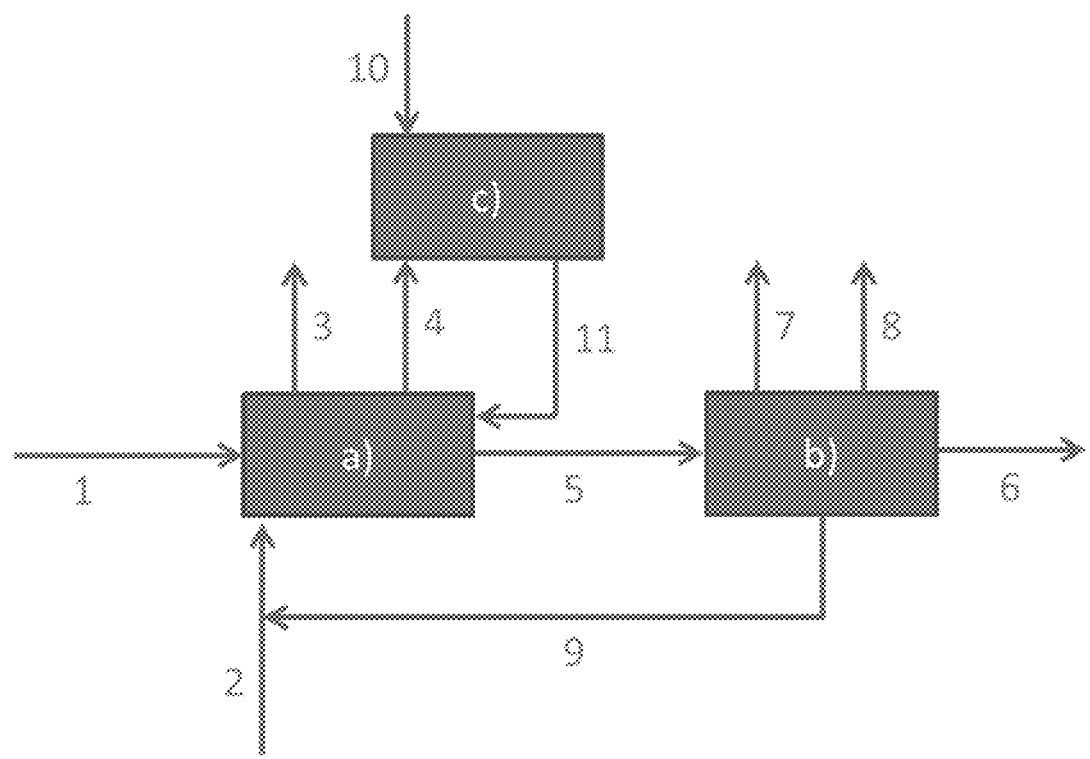
FIG. 2 has a particular arrangement of the esterification step with implementation of step c) for conversion of THF of the method according to the invention.

FIG. 2 has a particular arrangement of the esterification step with implementation of step c) for conversion of THF of the method according to the invention.

The esterification step a) is fed with the 1,4-butanediol feedstock (1), on the one hand, and by a flow of carboxylic acid (9) that is obtained from the pyrolysis step (b), the effluent (11) for conversion of the THF that is obtained from step c), and an addition of carboxylic acid (2), on the other hand. Step a) produces a 1,4-butanediol diester effluent (5) that is sent to the pyrolysis step b), a THF effluent (4) that is sent to step c) for conversion of THF, and a water effluent (3) that is eliminated from the method. The pyrolysis step b) is fed with the 1,4-butanediol diester effluent (5) that is obtained from step a) and produces a 1,3-butadiene effluent (7), with an effluent composed of light compounds (8) containing the cracking products of carboxylic acid, and a carboxylic acid flow (9) that is sent back to step a). During pyrolysis, a small proportion of coke is also produced, which is evacuated via the coke effluent (6). Step c) is fed with the THF effluent (4) obtained from step a) and with the acid anhydride effluent (10) and produces an effluent for conversion of THF (11) that is sent back to step a).

EXAMPLES

Example 1—Esterification of 2,3-Butanediol (for Comparison)

This example shows the performance of an esterification method that is implemented according to the teaching of the prior art.

The esterification of 2,3-butanediol is carried out in a closed stirred reactor, under the following conditions:
- A temperature of 110° C. (corresponds to the mean temperature of the reactive zone of the reactive distillation column al)).
- 6 mol of acetic acid per mol of 2,3-butanediol (corresponding to a large excess of acetic acid).
- Acid catalyst TA801 at 2.2 mol % in relation to 2,3-butanediol.

Figure 3:
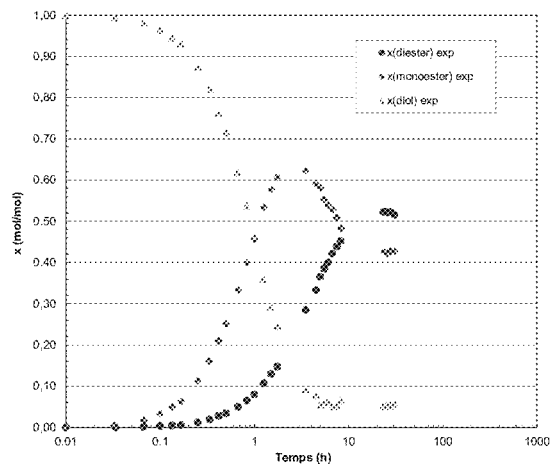
FIG. 3 shows conversion of 2,3-butanediol into monoester and diester over time is followed by gas chromatography.

The conversion of 2,3-butanediol into monoester and diester over time is followed by gas chromatography (FIG. 3). It should be noted that the kinetics of conversion of the RR, SS and RS forms of 2,3-butanediol are identical, and the proportions of the various diastereoisomers were added. It is possible to note that despite the presence of a large excess of acetic acid, the conversion of 2,3-butanediol is limited, which justifies carrying out reactive distillation in such a way as to shift the balance toward the formation of 2,3-butanediol diester.

Nevertheless, it is possible to note that the esterification kinetics is rather slow despite the presence of the acid catalyst, since it takes more than 20 hours to reach thermodynamic equilibrium.

Example 2—Esterification of 1,4-Butanediol (Invention)

This example shows the performance of an esterification method that is implemented according to the invention.

The esterification of 1,4-butanediol is carried out in a closed stirred reactor, under the following conditions:
- A temperature of 110° C. (corresponds to the mean temperature of the reactive zone of the reactive distillation column al)).
- 6 mol of acetic acid per mol of 1,4-butanediol (corresponding to a large excess of acetic acid).

Acid catalyst TA801 at 2.2 mol % in relation to 1,4-butanediol.

Figure 4:
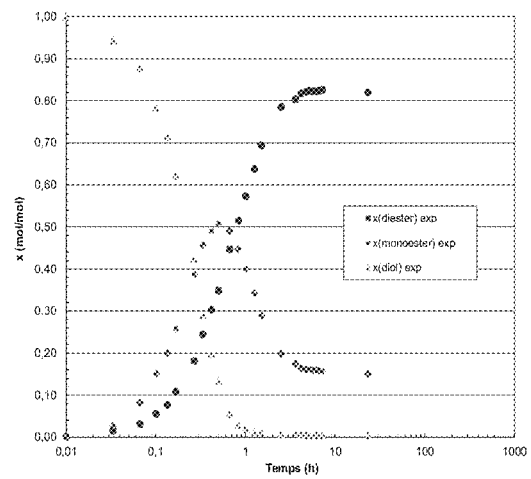
FIG. 4 shows conversion of 1,4-butanediol into monoester and diester over time is followed by gas chromatography.

The conversion of 1,4-butanediol into monoester and diester over time is followed by gas chromatography (FIG. 4). It is possible to note that, all other things being equal, the conversion of 1,4-butanediol is much greater than that of 2,3-butanediol. Industrially, this will be reflected by a reduction in the acetic acid/butanediol ratio and therefore by a reduction in operating and investment costs associated with the esterification step.

Furthermore, it is possible to note that the esterification kinetics of 1,4-butanediol is faster than that of 2,3-butanediol, since the thermodynamic equilibrium is reached in 3 hours in the case of the esterification of 1,4-butanediol, versus 20 hours in the case of the esterification of 2,3-butanediol. Industrially, this will be reflected by a reduction in dwell time within the reactive distillation column and therefore by a reduction in investment costs associated with this operation.

Example 3—Pyrolysis of 2,3-Butanediol Diacetate (for Comparison)

This example shows the performance of a pyrolysis method that is implemented according to the teaching of the prior art.

A feedstock that consists of 2,3-butanediol diacetate feeds a pyrolysis oven. The temperature of the pyrolysis oven is regulated in such a way as to obtain a reactor outlet temperature of 630° C. The flow rate of 2,3-butanediol diacetate is regulated to obtain a dwell time of between 0.9 and 1.5 seconds. The pyrolysis effluent is quickly cooled to 45° C. with a condenser placed right at the exit from the pyrolysis oven. The conversion of 2,3-butanediol diacetate varies between 96.5% and 99.1% based on the dwell time. The selectivity of transformation of 2,3-butanediol diacetate into 1,3-butadiene is between 78% and 82%. The selectivity of transformation of 2,3-butanediol diacetate into intermediate pyrolysis compounds varies between 17.2% and 20.0%. The selectivity of transformation of 2,3-butanediol diacetate into MEK varies between 0.9% and 1.8%. There is no other conversion product detected.

Among the intermediate pyrolysis compounds, some make it possible to increase the overall diolefin yield of the method if they are recycled in the step for pyrolysis and others do not. Methyl vinyl carbinol acetate (MVCA) and crotyl acetate (CA) make it possible to increase the butadiene yield if they are recycled in the step for pyrolysis, whereas this is not the case of methyl ethyl ketone enol acetate (MEKEA).

However, these intermediate pyrolysis compounds are isomers and therefore have very similar physico-chemical properties. Furthermore, these intermediate pyrolysis compounds are heavily diluted in carboxylic acid. It turns out that when the diol feedstock is a butanediol, regardless of the carboxylic acid being considered, the relative volatility between carboxylic acid and the intermediate pyrolysis compounds is very close to one. All of these elements together make the extraction of the intermediate pyrolysis compounds within the liquid pyrolysis effluent—for the purpose of maximizing the yield—very difficult.

Example 4—Pyrolysis of 1,4-Butanediol Diacetate (Invention)

This example shows the performance of a pyrolysis method that is implemented according to the invention.

A feedstock that consists of 1,4-butanediol diacetate feeds a pyrolysis oven. The temperature of the pyrolysis oven is regulated in such a way as to obtain a reactor outlet temperature of 630° C. The flow rate of 1,4-butanediol diacetate is regulated to obtain a dwell time of between 1 and 2 seconds. The pyrolysis effluent is quickly cooled to 45° C. with a condenser placed right at the exit from the pyrolysis oven. The conversion of 1,4-butanediol diacetate varies between 96.2% and 100% based on the dwell time. The selectivity of transformation of 1,4-butanediol diacetate into 1,3-butadiene is between 96.3% and 100%. The selectivity of transformation of 1,4-butanediol diacetate into 3-buten-1-ol (only intermediate pyrolysis compound) varies between 0% and 3.7%. A formation of THF is not observed. No other product is detected.

With this example, we will demonstrate that the use of 1,4-butanediol as a feedstock of a method for esterification and pyrolysis according to the invention for the production of 1,3-butadiene offers the advantage of having a higher molar yield of butadiene and of forming fewer by-products.

Example 5—Production of Butadiene from a 1,4-Butanediol Feedstock (Invention)

This example illustrates the production of 1,3-butadiene from a 1,4-butanediol feedstock by the method according to the invention, in its variant with (variant 5-a) and without (variant 5-b) implemented in step c).

Variant 5-a (Invention), without Implementation of Step c) for Conversion of THF The table below provides the flow rates and the composition of the various flows within the method according to the invention, with the numbering of the flows being identical to that of FIG. 1.

The 1,4-butanediol feedstock (1) that primarily contains 1,4-butanediol, but also 3.7% by weight of water, feeds an esterification step a). This esterification step a) is furthermore fed with the flow (9) that is obtained from the pyrolysis step b) and that consists primarily of acetic acid and with the flow (2) of pure acetic acid that makes it possible to compensate for the losses of acetic acid within the method. This esterification step a) furthermore produces the water flow (3) that is eliminated from the method, the THF flow (4a) that is eliminated from the method, and the 1,4-butanediol diester flow (5) that is sent to the pyrolysis step b).

The pyrolysis step b) produces a 1,3-butadiene flow (7), a flow (8) of incondensable products obtained from the pyrolysis of acetic acid, and a flow (9) that consists primarily of acetic acid and that is sent back to the esterification step a).

Coke is also produced during pyrolysis, which is eliminated by the flow (6) during the regeneration of the pyrolysis oven.

| | Flow | | | | | | | | |
|---|---|---|---|---|---|---|---|---|---|
| | (1) | (2) | (3) | (4a) | (5) | (6) | (7) | (8) | (9) |
| Flow Rate (kg/h) | 9358 | 572 | 3907 | 158 | 17250 | 344 | 5186 | 335 | 11384 |
| Composition (% by Weight) | | | | | | | | | |
| 1,4-Butanediol | 96.3 | — | — | — | — | — | — | — | — |
| Water | 3.7 | — | 100 | — | — | — | — | — | — |
| Acetic Acid | — | 100 | — | — | 0.14 | — | — | — | 98.94 |
| THF | — | — | — | 100 | — | — | — | — | 0.06 |
| Diester | — | — | — | — | 99.78 | — | — | — | — |
| Monoester | — | — | — | — | 0.08 | — | — | — | — |
| 1,3-Butadiene | — | — | — | — | — | — | 100 | — | — |
| Intermediate Compound | — | — | — | — | — | — | — | — | 1.00 |
| Incondensable Products | — | — | — | — | — | — | — | 100 | — |
| Coke | — | — | — | — | — | 100 | — | — | — |

Thus, 0.57 ton of butadiene per ton of 1,4-butanediol is produced by the method according to the invention, or a yield of 95.9% of the stoichiometric yield. The yield loss stems from various undesirable reactions:

- The production of THF by dehydration of 1,4-butanediol in the esterification step a),
- The production of THF by hydrolysis of the intermediate pyrolysis compound, when the latter is not isolated but directly recycled to the esterification step a),
- The production of THF by pyrolysis of 1,4-butanediol monoester in the pyrolysis step b),
- And finally the production of coke.

Variant 5-b (Invention), with Implementation of Step c) for Conversion of THF

The table below provides the flow rates and the composition of the various flows within the method according to the invention, with the implementation of step c) for conversion of THF, with the number of flows being identical to that of FIG. 2.

The 1,4-butanediol feedstock (1) that primarily contains 1,4-butanediol, but also 3.7% by weight of water, feeds an esterification step a). This esterification step a) is furthermore fed with the flow (9) that is obtained from the pyrolysis step b) and that primarily consists of acetic acid, and with the flow (2) of pure acetic acid that makes it possible to compensate for the losses of acetic acid within the method. This esterification step a) furthermore produces the water flow (3) that is eliminated from the method, the THF flow (4) that is sent to step c) for conversion of THF, and the 1,4-butanediol diester flow (5) that is sent to the pyrolysis step b).

Step c) is fed with the flow (4) that is obtained from step a) and with the flow (10) of acetic anhydride and produces a flow (11) that is sent back to the esterification step a).

The pyrolysis step b) produces the 1,3-butadiene flow (7), a flow (8) of incondensable products obtained from the pyrolysis of acetic acid, and a flow (9) that consists primarily of acetic acid and that is sent back to the esterification step a).

Coke is also produced during the pyrolysis, which is eliminated by the flow (6) during the regeneration of the pyrolysis oven.

| | Flow | | | | | | | | | | |
|---|---|---|---|---|---|---|---|---|---|---|---|
| | (1) | (2) | (3) | (4) | (5) | (6) | (7) | (8) | (9) | (10) | (11) |
| Flow Rate (kg/h) | 9358 | 285 | 3901 | 155 | 17623 | 352 | 5302 | 342 | 11626 | 255 | 410 |
| Composition (% by Weight) | | | | | | | | | | | |
| 1,4-Butanediol | 96.3 | — | — | — | — | — | — | — | — | — | — |
| Water | 3.7 | — | 100 | — | — | — | — | — | — | — | — |
| Acetic Acid | — | 100 | — | — | 0.14 | — | — | — | 99 | — | — |
| Acid Anhydride | — | — | — | — | Traces | — | — | — | — | 100 | 9.7 |
| THF | — | — | — | 100 | — | — | — | — | — | — | 0.7 |
| Diester | — | — | — | — | 99.86 | — | — | — | — | — | 89.6 |
| Monoester | — | — | — | — | Traces | — | — | — | — | — | — |
| 1,3-Butadiene | — | — | — | — | — | — | 100 | — | — | — | — |
| Intermediate Compound | — | — | — | — | — | — | — | — | 1 | — | — |
| Incondensable Products | — | — | — | — | — | — | — | 100 | — | — | — |
| Coke | — | — | — | — | — | 100 | — | — | — | — | — |

Thus, 0.59 ton of butadiene per ton of 1,4-butanediol is produced by the method according to the invention, with a step for conversion of THF, or a yield of 98% of the stoichiometric yield. Furthermore, it will be possible to note that in comparison to Example A, the performance of the esterification step a) has been improved, owing to the recycling in step a) of the flow (11) also containing the acetic anhydride that is unconverted at step c. Furthermore, since there is no longer any 1,4-butanediol monoester in the flow (5) that is sent to step b), there is therefore no longer any THF formation in the pyrolysis step c).

The invention claimed is:

1. A method for conversion of a 1,4-butanediol feedstock, said method comprising at least:
   a) esterification of the 1,4-butanediol feedstock and a flow comprising more than 50% by weight part carboxylic acid to produce an effluent, and separating the effluent from the reaction section into at least one 1,4-butanediol diester effluent, a water effluent, and a carboxylic acid effluent in at least one separation section, wherein the esterification in said reaction section is implemented in the presence of an acid catalyst at a pressure of between 0.01 and 1.0 MPa and at a flow rate of moles of diol to moles of catalyst in said reaction section of between 0.05 and 25 $h^{-1}$; and
   b) pyrolysis of said at least one 1,4-butanediol diester effluent to produce a pyrolysis effluent, wherein said pyrolysis also comprises at least one separation section wherein said pyrolysis effluent is cooled to a temperature that is less than 100° C. to produce at least one liquid pyrolysis effluent and one vapor pyrolysis effluent, wherein said vapor pyrolysis effluent is compressed and/or cooled to condense 1,3-butadiene into a 1,3-butadiene effluent, and separating the liquid pyrolysis effluent by simple distillation to produce a carboxylic acid flow and a 3-buten-1-ol ester flow as a carboxylic acid/3 buten-1-ol ester azeotrope.

2. The method according to claim 1, wherein the flow of carboxylic acid comprises the carboxylic acid effluent that is obtained from the separation section of a).

3. The method according to claim 1, wherein the flow of carboxylic acid comprises external carboxylic acid.

4. The method according to claim 1, wherein said reaction section of a) is implemented in a reactive distillation column, in which the 1,4-butanediol feedstock is introduced into an upper part of the column, and the carboxylic acid is introduced into a lower part of the column, with the ratio of the molar flow rates of 1,4-butanediol and carboxylic acid being between 2 and 6.

5. The method according to claim 1, wherein the carboxylic acid is formic acid, acetic acid, propanoic acid, butanoic acid, or benzoic acid.

6. The method according to claim 5, wherein the carboxylic acid is acetic acid.

7. The method according to claim 6, wherein said separation in a) comprises heterogeneous azeotropic distillation using a driver.

8. The method according to claim 1, wherein said 3-buten-1-ol ester flow is recycled to pyrolysis b) with the 1,4-butanediol diester.

9. The method according to claim 1, wherein a THF effluent is separated from the effluent of said reaction section of a).

10. The method according to claim 9, further comprising c) converting the THF effluent into 1,4-butanediol diester with an acid anhydride effluent in the presence of an acid catalyst to produce an effluent.

11. The method according to claim 10, wherein the effluent that is obtained from c) conversion of THF into 1,4-butanediol diester is sent directly to b) pyrolysis of 1,4-butanediol diester or to a dedicated step for pyrolysis producing more butadiene.

12. The method according to claim 10, wherein the effluent that is obtained from c) conversion of THF into 1,4-butanediol diester is sent back to a) esterification of the 1,4-butanediol feedstock.

13. A method for conversion of a 1,4-butanediol feedstock, said method comprising at least:
   a) esterification of the 1,4-butanediol feedstock and a flow comprising more than 50% by weight part carboxylic acid to produce an effluent, and separating the effluent from the reaction section into at least one 1,4-butanediol diester effluent, a water effluent, and a carboxylic acid effluent in at least one separation section, wherein the esterification in said reaction section is implemented in the presence of an acid catalyst at a pressure of between 0.01 and 1.0 MPa and at a flow rate of moles of diol to moles of catalyst in said reaction section of between 0.05 and 25 $h^{-1}$; and
   b) pyrolysis of said at least one 1,4-butanediol diester effluent to produce a pyrolysis effluent, wherein said pyrolysis also comprises at least one separation section wherein said pyrolysis effluent is cooled to a temperature that is less than 100° C. to produce at least one liquid pyrolysis effluent and one vapor pyrolysis effluent, wherein said vapor pyrolysis effluent is compressed and/or cooled to condense 1,3-butadiene into a 1,3-butadiene effluent, wherein the liquid pyrolysis effluent is separated by distillation with a change in pressure to produce a carboxylic acid flow and a 3-buten-1-ol ester flow.

14. The method according to claim 1, wherein the flow of carboxylic acid comprises said carboxylic acid flow that is obtained from the liquid pyrolysis effluent.

* * * * *